United States Patent
Jordan

(10) Patent No.: US 6,808,535 B1
(45) Date of Patent: Oct. 26, 2004

(54) STENT FOR KEEPING OPEN TUBULAR STRUCTURES

(75) Inventor: Andreas Jordan, Berlin (DE)

(73) Assignee: Magforce Applications GmbH, Berlin (DE)

(*) Notice: Subject to any disclaimer, the term of this patent is extended or adjusted under 35 U.S.C. 154(b) by 0 days.

(21) Appl. No.: 09/959,035

(22) PCT Filed: Apr. 28, 2000

(86) PCT No.: PCT/DE00/01415
§ 371 (c)(1),
(2), (4) Date: Dec. 27, 2001

(87) PCT Pub. No.: WO00/66192
PCT Pub. Date: Nov. 9, 2000

(30) Foreign Application Priority Data

Apr. 30, 1999 (DE) .......................... 199 21 088

(51) Int. Cl.⁷ .................................................. A61F 2/06
(52) U.S. Cl. ..................... 623/1.34; 623/1.45; 623/1.46
(58) Field of Search ................................ 623/1.34, 1.46, 623/1.45, 1.15, 1.32, 1.42, 1.43, 1.41, 1.48; 606/191–198

(56) References Cited

U.S. PATENT DOCUMENTS

| 3,741,198 A | * | 6/1973 | Burton ........................ 600/431 |
| 4,101,435 A | * | 7/1978 | Hasegawa et al. ........ 252/62.53 |
| 4,839,215 A | * | 6/1989 | Starling et al. .............. 428/131 |
| 5,053,048 A | * | 10/1991 | Pinchuk ...................... 623/1.43 |
| 5,081,997 A | * | 1/1992 | Bosley et al. ................ 600/458 |
| 5,163,958 A | * | 11/1992 | Pinchuk ....................... 606/194 |
| 5,178,618 A | | 1/1993 | Kandarpa |
| 5,197,978 A | | 3/1993 | Hess |
| 5,349,957 A | * | 9/1994 | Yudelson ..................... 600/414 |
| 5,565,215 A | * | 10/1996 | Gref et al. ................... 424/501 |
| 5,571,166 A | | 11/1996 | Dinh et al. |
| 5,599,576 A | * | 2/1997 | Opolski ....................... 427/2.3 |
| 5,840,009 A | | 11/1998 | Fischell et al. |
| 5,840,387 A | * | 11/1998 | Berlowitz-Tarrant et al. ........................... 623/1.1 |
| 5,843,172 A | * | 12/1998 | Yan ............................. 606/191 |
| 5,908,410 A | * | 6/1999 | Weber et al. ................ 604/523 |
| 5,921,933 A | * | 7/1999 | Sarkis et al. ................ 600/459 |
| 5,935,506 A | * | 8/1999 | Schmitz et al. ............. 623/900 |
| 5,972,027 A | * | 10/1999 | Johnson ...................... 623/1.42 |
| 6,143,370 A | * | 11/2000 | Panagiotou et al. ........ 427/422 |
| 6,280,385 B1 | * | 8/2001 | Melzer et al. ............... 600/423 |

FOREIGN PATENT DOCUMENTS

| DE | 197 26 282 | 12/1998 | |
| WO | WO 9710011 A1 | * 3/1997 | ........... A61L/27/00 |
| WO | WO 9958083 A1 | * 11/1999 | ............. A61F/2/04 |

* cited by examiner

Primary Examiner—Julian W. Woo
Assistant Examiner—Jessica R. Baxter
(74) Attorney, Agent, or Firm—Webb Ziesenheim Logsdon Orkin & Hanson, P.C.

(57) ABSTRACT

A stent made of metallic and/or non-metallic material that can be implanted into tubular structures or other body cavities is coated with nanoscale particles that consist of a paramagnetic core and at least one shell adsorbed to it which is durably bonded to the stent surface. This coating makes it possible to selectively and homogeneously heat up the implant by applying an alternating magnetic field with a clinically tolerable combination of field strength and frequency, thereby achieving high power absorption and, on the one hand, a temperature level that enhances the growing-in of the implant by enhancing cell proliferation, on the other hand, a temperature range in which a restenosed implant can be regenerated. Also, it facilitates position detection.

14 Claims, No Drawings

STENT FOR KEEPING OPEN TUBULAR STRUCTURES

BACKGROUND OF THE INVENTION

1. Field of the Invention

This invention relates to a stent for keeping open tubular structures in the human body and to prevent restenosis by action eat.

2. Brief Description of the Prior Art

When treating the occurrence of stenoses in tubular structures such as vessels, the urinary tract and the like, or vascular aneurysms, stents or intraluminal tubes, i.e. generally tube-shaped supports made of metal and/or a polymer are implanted into the respective hollow viscus to keep the contracted structures open. The problem of using such implants is, however, that restenosis or an obstruction occurs soon after implantation, requiring another highly risky and costly surgical operation. When restenosis of cardiovascular stents occurs, an extensive bypass operation quite frequently is the only option.

Special catheters and microtools or laser tools are typically used to mechanically lay open the obstructive area of the stent under angiographic monitoring. Such regeneration, however, can be done twice at best. After that the stent support has to be replaced by a new implant.

Use of radioactive stents has been proposed to prevent the disadvantages mentioned above (U.S. Pat. No. 5,840,009, as re-embedding of endothelia or smooth muscle cells within the stent would not occur in the near range of radiation. However, exact dosage of radiation is difficult, and its cytotoxic effects are still uncertain.

Furthermore, stents have been described that are coated with anti-adhesion molecules (DE 197 13 240), fibrin/fibrinogen (U.S. Pat. No. 5,660,873), silicone (U.S. Pat. No. 5,330,500), or carbon (U.S. Pat. No. 5,163,958) or that come with a therapeutic delivery system (U.S. Pat. No. 5,439,446) to prevent restenosis.

Also known are stents made of a heat recoverable material (U.S. Pat. No. 5,197,978) that are connected to an electric heater, are introduced into a stenosed area of a hollow viscus and thermally dilated using a balloon catheter and can later be recovered to their original configuration. Finally publications (U.S. Pat. No. 5,178,618) describe expandable stents that can be heated to temperatures between 50° C. and 100° C. using external radiofrequency waves for ducting and stenosing tubular structures in the human body. Generation of heat in the stent material prevents proliferation of smooth muscle cells which are assumed to be responsible for restenosis of the stent and the resulting adverse consequences described at the outset.

Regeneration of electroconductive iron-containing restenosed stents in the body faces the setback that they only heat up at a relatively high field strength-frequency combination due to hysteresis and eddy-current losses that result in power absorption in the electroconductive tissue at the body surface and thus undesirable overheating of the peripheral adipose tissue and other uninvolved tissue. Regenerating metallic and non-metallic implants using heat has thus been unfeasible.

SUMMARY OF THE INVENTION

It is therefore the problem of this invention to provide a stent of the above type that, both in its metallic and non-metallic designs, can be selectively heated as desired to prevent restenosis or obstruction and to facilitate the stent's growing into the respective hollow viscus.

This problem is solved according to the invention by providing a stent consisting of a metallic and/or non-metallic material and coated with nanoscale particles that comprise a paramagnetic core and a covering that can adsorb to the stent for position detection by MR tomography and for homogeneous and controlled heating and power absorption in an alternating magnetic field with a specific field strength and frequency suitable for clinical use.

The stent implant according to the invention, in metallic or non-metallic design, to the surface of which nanoscale particles are bonded in an even distribution pattern, makes it possible to set a controllable temperature that is restricted to the stent and slightly above the normal physiological temperature in a field strength and frequency range suitable for clinical use, thereby ensuring fast growing-in of the implant through enhancing the proliferation of new cells and regeneration of the restenosed stent at a temperature range from 50 to 60° C. Due to their coating with nanoscale particles, both metallic and non-metallic designs of the implants are capable of high power absorption at field strengths below 10 kA/m and in a frequency range suitable for clinical use. Also, the stents heat up evenly. In addition, the provided coating allows position detection of the stent using MR tomography, no matter which implant material is used.

In a further improvement of the invention, said nanoscale particles consist of a core that contains, preferably consists of, ferromagnetic, ferrimagnetic, or preferably supramagnetic iron oxide and a covering made of at least one shell-adsorbing to the core. Said shell(s) comprise(s) reactive groups that can form cationic groups for permanent bonding of the outer shell to the surface of the stent. Said nanoscale particles are produced using known methods, such as the methods described in German laid-open patent publications nos. 195 15 820, 196 14 136, and 197 26 282.

DETAILED DESCRIPTION OF THE INVENTION

More specifically, the invention is a stent for keeping open tubular structures and restenosis prevention by heating said stent. The stent includes a tube-shaped support made of a metallic and/or non-metallic material coated with nanoscale particles each of which includes a paramagnetic core and a covering that can adhere to said stent for position detection by MR tomography and for homogeneous and controlled heating and power absorption in an alternating magnetic field having a specific field strength and frequency suitable for clinical use.

Each nanoscale particle includes a ferromagnetic, ferrimagnetic or supramagnetic core and at least one shell surrounding said core that can absorb to said core. The shell comprises reactive groups capable of forming cationic groups that are degraded so slowly by body tissue that the outer shell durably bonds to the surface of said stent made of metallic and/or non-metallic material.

The core of each nanoscale particle can consist of (1) pure iron oxide that includes magnetite and/or maghemite; (2) pure Fe (II): Fe (III) iron particles at ratios from 1:1 to 1:3; or (3) iron containing mixed oxides having a content of non-ferrous metallic atoms desirably not greater than 70% and more desirably not greater than 35% of metallic atoms.

The reactive groups can include monomeric aminosilanes and carboxyl groups. The shell can absorb to the stent through microemulsion or tenside-mediated reactions.

The covering on each nanoscale particle can further include another, outer shell of nanoscale particles for attachment of biomolecules. The biomolecules can be one of fibrinolytic or anti-coagulant enzymes such as protease, heparin or a heparin derivative. The average diameter of the nanoscale particles is desirably smaller than 100 nm, more desirably smaller than 50 nm and most desirably smaller than 30 nm. The average particle size is desirably between 1 and 40 nm and, more desirably between 3 and 30 nm.

The stent can be configured to be heated up in an alternating magnetic field for producing rapid gradient fields within NMR tomography.

In a test arrangement, the fibrinogen portion of a fibrin-fibrinogen solution was thoroughly mixed with 15 mg/ml of a preparation of nanoscale particles coated with aminosilane. A commercially available endovascular stent of an expandable metallic design was then dipped into the fibrin-fibrinogen solution prepared as described above. The coating of nanoscale particles obtained in this way remained stable on the wire fabric of the stent when it was subsequently dilated using a balloon catheter. The coated stent was inserted into a tube filled with water and exposed to an alternating magnetic field with a strength of 10 to 18 kA/m and at a frequency of 100 kHz. An uncoated stent was also exposed to the alternating field for comparison. It was found that the coated stent absorbs sufficient power and heats up as required for regeneration of restenosed stents at a field strength of just 10 kA/m. The uncoated stent, however, is not heated up in this clinically relevant field strength range in which no undesired heating up of other tissue occurs. The uncoated stent reaches a sufficiently high power absorption and the associated heating up of the stent and other tissues at field strengths of 15 kA/m and more. This means that power absorption of the stent coated with nanoscale particles at 10 kA/m matches that of the uncoated stent at 15 kA/m.

Based on the power absorption (W/g) calculated as a function of field strength and frequency and the perfusion rate in the vessel or hollow viscus in which the stent is implanted, the temperature-time curve of heating up the stent in the human body by applying an alternating magnetic field at a specific frequency can be calculated. In practical use, a fiber-optic temperature-measuring probe is inserted into the stent via a stent implantation catheter and monitored by angiography so that the temperature is checked while said alternating magnetic field is applied. The implanted stent is heated to a temperature slightly above the normal physiological level to accelerate its growing-in by stimulating cell growth on the surface of the implant. If the stent implant has to be regenerated later due to restenosing, perfusion in the stent area is determined prior to applying the alternating magnetic field. The exact position of the implant can be determined by contrast media radiography or NMR tomography.

I claim:

1. A stent for keeping open tubular structures and restenosis prevention by heating, said stent comprising a tube-shaped support made of one of a metallic and a non-metallic material coated with nanoscale particles, with each nanoscale particle including a paramagnetic core and at least one shell that adheres to said stent for position detection by MR tomography and for homogeneous and controlled heating and power absorption in an alternating magnetic field with a specific field strength and frequency suitable for clinical use, wherein:

each nanoscale particle consists of one of a ferromagnetic, ferrimagnetic and supramagnetic core;

said shell surrounds and adsorbs to said core; and said shell comprises reactive groups formed from monomeric aminosilanes capable of forming cationic groups that are degraded so slowly by body tissue that said shell durably bonds to said stent when said stent is in contact with the body tissue.

2. The stent according to claim 1, wherein the core of each nanoscale particle consists of pure iron oxide that includes at least one of magnetite and maghemite.

3. The stent according to claim 1, wherein the core of each nanoscale particle consists of pure Fe (II):Fe (III) iron oxide particles at ratios from 1:1 to 1:3.

4. The stent according to claim 1, wherein the core of each nanoscale particle consists of iron-containing mixed oxides having a content of non-ferrous metallic atoms not greater than 70% of metallic atoms.

5. The stent according to claim 1, further including another shell of said nanoscale particles for attachment of biomolecules.

6. The stent according to claim 5, wherein the biomolecules arc one of fibrinolytic and anti-coagulant enzymes.

7. The stent according to claim 6, wherein the one of the fibrinolytic and anti-coagulent enzymes are one of a protease, heparin and a heparin derivative.

8. The stent according to claim 1, wherein the average diameter of each nanoscale particle is smaller than 100 nm.

9. The stent according to claim 8, wherein the average diameter of each nanoscale particle is between 1 nm and 40 nm.

10. The stent according to claim 9, wherein the average diameter of each nanoscale particle is between 3 nm and 30 nm.

11. The stent according to claim 8, wherein the stent is designed to be heated up by an alternating magnetic field for producing rapid gradient fields within NMR tomography.

12. The stent according to claim 8, wherein the average diameter of each nanoscale particle is smaller than 50 nm.

13. The stent according to claim 8, wherein the average diameter of each nanoscale particle is smaller than 30 nm.

14. The stent according to claim 13, wherein the core of each nanoscale particle consists of iron-containing mixed oxides having a content of non-ferrous metallic atoms not greater than 35% of metallic ions.

* * * * *

UNITED STATES PATENT AND TRADEMARK OFFICE
CERTIFICATE OF CORRECTION

PATENT NO. : 6,808,535 B1
DATED : October 26, 2004
INVENTOR(S) : Jordan

It is certified that error appears in the above-identified patent and that said Letters Patent is hereby corrected as shown below:

Column 4,
Line 33, "arc one of" should read -- are one of --
Line 52, "according to claim 13" should read -- according to claim 1 --

Signed and Sealed this

Tenth Day of May, 2005

JON W. DUDAS
*Director of the United States Patent and Trademark Office*